United States Patent [19]

Callahan

[11] Patent Number: 4,724,845
[45] Date of Patent: Feb. 16, 1988

[54] METHOD OR SYSTEMS OF DETERMINING PHYSIOLOGICAL STATUS

[75] Inventor: Richard A. Callahan, S. Pasadena, Calif.

[73] Assignee: Vestar Research, Inc., Pasadena, Calif.

[21] Appl. No.: 763,753

[22] Filed: Aug. 5, 1985

Related U.S. Application Data

[63] Continuation of Ser. No. 673,414, Nov. 20, 1984, abandoned, which is a continuation of Ser. No. 407,922, Aug. 13, 1983, abandoned.

[51] Int. Cl.⁴ ............................................. A61B 5/00
[52] U.S. Cl. ................................................... 128/718
[58] Field of Search .................. 128/716, 718, 202.12, 128/208.11, 707

[56] References Cited

U.S. PATENT DOCUMENTS

| | | | |
|---|---|---|---|
| 2,663,282 | 12/1953 | Ingle | 119/29 |
| 2,970,041 | 1/1961 | Burlis et al. | 128/718 X |
| 3,045,665 | 7/1962 | Moyat | 128/718 |
| 3,401,683 | 9/1968 | Webb et al. | 128/718 |
| 3,523,529 | 8/1970 | Kissen | 128/718 |
| 3,698,384 | 10/1972 | Jones | 128/718 |
| 3,799,149 | 3/1974 | Rummel et al. | 128/2.07 |
| 4,299,235 | 11/1981 | Cohen | 128/718 |

FOREIGN PATENT DOCUMENTS 0028209 10/1980 European Pat. Off. .
0083848 12/1982 European Pat. Off. .

Primary Examiner—Edward M. Coven
Attorney, Agent, or Firm—Lyon & Lyon

[57] ABSTRACT

A method for determining metabolic status of any organism is disclosed. The method is based on determining the changes in rate of oxygen consumption as a function of varying stress levels, and particularly in response to varying the levels of ambient oxygen supply to the organism. Typically, the stress variation is imposed against a backdrop of constant second stress applied to the same organism.

28 Claims, 7 Drawing Figures

BASELINE OXYGEN CONSUMPTION RATE AT TWO EXERCISE LEVELS.

METHOD OR SYSTEMS OF DETERMINING PHYSIOLOGICAL STATUS

This application is a continuation of application Ser. No. 673,414, filed 11/20/84, abandoned. This is a continuation of application Ser. No. 407,922, filed Aug. 13, 1983 now abandoned.

BACKGROUND OF THE INVENTION

This invention relates to apparatus and methods for determining physiological or metabolic status of an organism by measuring and comparing effects of applied metabolic stresses. More specifically, this invention includes an apparatus and a method for monitoring the adaptive control of oxygen consumption to measured changes in stress. Data presented in this invention indicate that monitoring this adaptive process is an efficient means of delimiting the metabolic capacity of the organism.

It has long been thought desirable to obtain a general measure of physical health by assessing the overall metabolic capability of an organism. Metabolic tests, for example, have been a part of standard physical examinations for presumably healthy individuals for years. In contrast to attempts to diagnose specific illnesses or dysfunctions, these measurements attempt to assess the efficiency and general integrity of the physiological systems of the organism as a whole. For example, in mammalian systems, the relationship of the respiratory, cardiopulmonary, and even endocrine systems, as well as their individual capacities and status, impacts on the overall well-being of the mammal. All organisms can be assumed to be in better or poorer health depending on the individual status and integration of a number of metabolic systems.

It is, of course, desirable to have available a method for quantification of what might loosely be called good or poor health or efficiency level for the organism. There is a particular interest in assessing the effects of externally imposed environmental factors on the organism and evaluating the effects of potentially toxic substances. It is now generally thought that certain environmental factors, such as, for example, poor air quality, certain chemicals, which are found as contaminants in food, water or air, and general dietary factors, which may produce effects which are not sufficiently acute to result in measurable specific symptoms except in isolated individuals, may, in fact, cause a general diminution of well being in the population as a whole. Also, it is clear that there are potential toxic effects of medications which are associated with only vague symptoms, such as moderate discomfort or nausea, which do not uniformly impact all members of the subject population. These seem not at present to be amenable to effective pretesting, because of a lack of a quantitative system of measuring impact on the overall organism. In addition, it would be desirable to test the direct effects of drugs at as low a dosage level as is possible, and to determine the physical condition of healthy animals and human beings.

The present invention provides for quantitative assessment of these factors by using adaptive respiratory capacity as a measure of overall metabolic status. The adaptive respiratory capacity of an organism is measured by ascertaining the rate of consumption of oxygen as a function of stress in various forms.

This method employs a respirometer of a design which, itself, represents an improvement over the presently available means for assessing oxygen uptake in subject organisms, and which has also a means for applying and varying stress to the subject organism. Many devices have been designed to monitor the respiratory rate of a subject while under situations of controlled environmental situations. However, devices which measure metabolic capacity by measuring the adaptive respiratory responses of organisms to sequentially applied quantitatively measured stresses do not exist. Since most respiratory monitoring devices communicate with ambient air, they do not readily facilitate reduced oxygen pressure as one possible form of environmental stress. For example, U.S. Pat. No. 3,401,683 to Webb discloses an apparatus wherein the subject wears a helmet which causes exhaled gases to be drawn into the monitoring device. Thus, if testing at reduced $pO_2$ is desired, the entire monitoring device must be enclosed in the test chamber. In U.S. Pat. No. 3,523,529 and U.S. Pat. No. 3,507,146, devices are disclosed which are worn by the subject and measure oxygen uptake through a breathing mask or similar apparatus attached to the nose and mouth in order to isolate the exhaled air. Resulting metabolic rate calculations must take into account effects of such cumbersome monitoring devices. Because of the above considerations, present systems severely limit the variety of organisms which may be subjected to metabolic analysis by respiratory techniques, do not measure the organisms adaptive respiratory response to stress and do not use the adaptive responses as a means for measuring metabolic disfunction. The present invention offers the capacity to measure not simply the oxygen consumption of any organism which is capable of respiration, but also provides a means to control stress levels by adjusting the oxygen concentration, increasing temperature, exercise intensity, or other physical parameters and in these fashions measure the adaptive respiratory response of the organism to these stress and use these responses to detect changes in metabolic function.

SUMMARY OF THE INVENTION

The present invention relates to a method of determining metabolic status by generating a pattern of adaptive respiratory response consisting of the rate of oxygen consumption of a subject organism at discrete and measured levels of stress. In preferred embodiments, said stress takes the form of a series of oxygen tensions and discrete levels of exercise.

In a second aspect, the invention concerns an apparatus for carrying out the method of the invention. The apparatus is characterized by the use of a feedback circuit to control the generation of oxygen by an electrolytic cell, thus enabling the measurement of oxygen uptake by measuring the oxygen generated to maintain a constant level of oxygen, which is controlled at the option of the investigator. The oxygen monitoring and generation modules are attached to a biological chamber which can be of many designs. The characteristics of the apparatus are such as to impose a measured stress on the tested animals while maintaining other environmental parameters constant.

DETAILED DESCRIPTION OF THE INVENTION

Definitions

Figure 1:
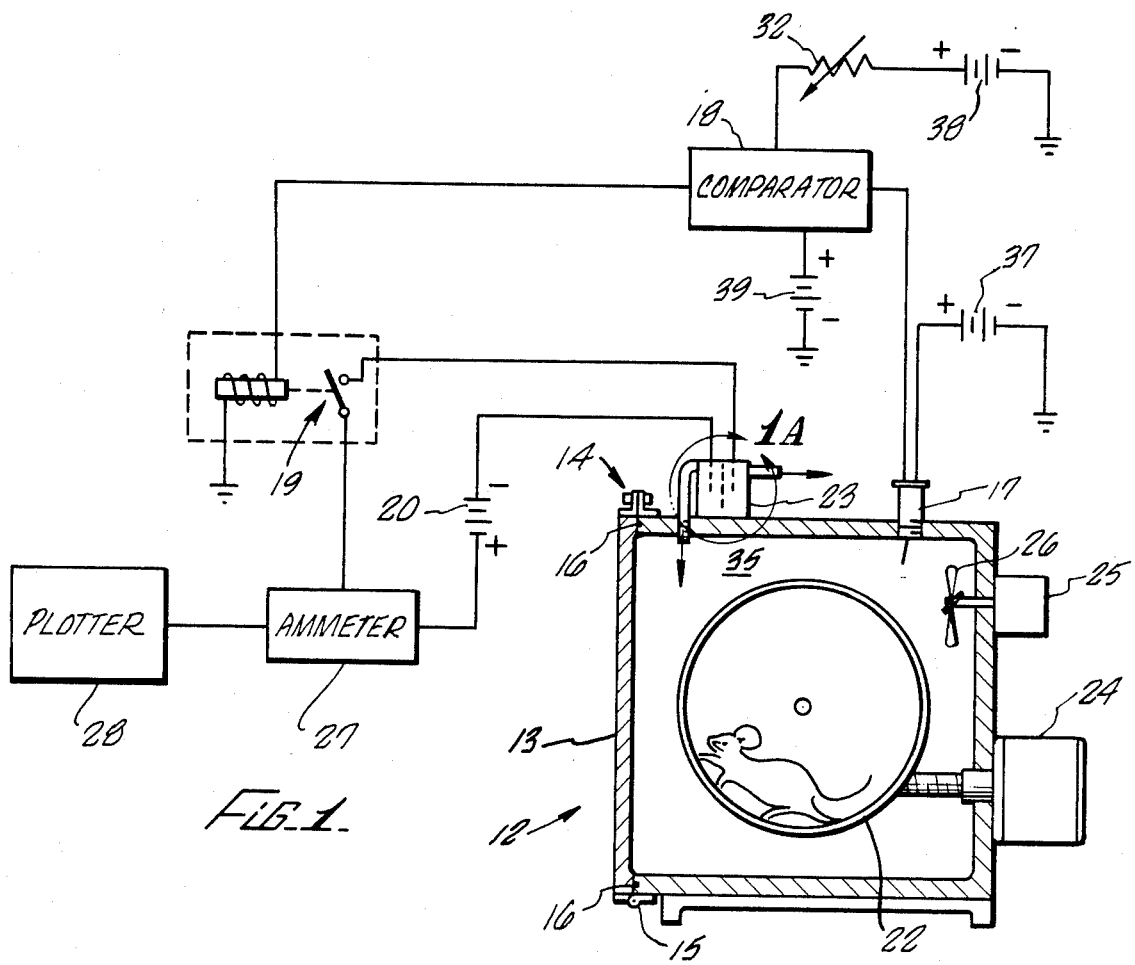
FIG. 1 is a schematic of a preferred embodiment of the apparatus of the invention.

As used herein, "biological chamber" or "testing chamber" refers to an enclosed chamber, which is optionally capable of motion to provide physical activity demand on the subject, which will contain the organism to be tested for metabolic status. The chamber has interfaces with its surroundings which permit exchange of materials only in a limited way while the organism is being tested, i.e., oxygen is permitted to enter the chamber from the electrolysis cell used to generate oxygen in the experiment or from other oxygen generating means, and, carbon dioxide is absorbed by a carbon dioxide absorbant in conjunction with the chamber. Other chambers suitable for testing senescent biological materials such as eggs, neonates, tissue cultures, seeds, plant materials or microbes are envisioned which would substitute the exercising stress with an appropriate alternative such as heat, or radiation.

"Metabolic or physiological status" refers to the total physiological well being of the subject. It has meaning in the scope of this invention only in a comparative sense—i.e., the metabolic status of a "healthy" subject can be compared to an unhealthy one of the same species; that of a drugged subject with an undrugged one.

"$pO_2$" or "oxygen concentration" refers to the partial pressure of the oxygen in the testing chamber. Strictly speaking, of course, $pO_2$ should be expressed in pressure units such as atmospheres or torr, and the invention is meant to include those situations wherein the total ambient pressure in the testing chamber is not equal to approximately one atmosphere. However, in practical usage, the total pressure inside the testing chamber will be on the order of one atmosphere or 760 torr, and the $pO_2$ will be expressed, more conveniently, in terms of mole percentage of total gas phase, i.e., oxygen concentration as a % of total moles. This facilitates comparison with value normally found in air, which is ordinarily 21% oxygen, approximately. Under atmospheric conditions, this would correspond to a partial pressure of 160 torr.

"Failure" means a discernible change in the performance of the experimental subject such as, in the case of a mammal, a loss of motor coordination, or an inability to perform minimal exercise such as maintenance against the turning motion of the testing chamber in the preferred embodiment of the invention set forth below. Failure may be defined to be a cessation of respiration in the case of senescent subject matter, such as seeds, eggs or plant materials, when tested against a physical gradient such as heat. Therefore the term failure is simply an endpoint in the experimental protocol at which the organism can no longer accommodate the stress.

"Baseline" means that rate of oxygen consumption which is consistently maintained by a subject organism under normal oxygen pressure and consistent exercise or stress demands.

"Breakpoint" refers to the pressure of oxygen ($pO_2$) at which the baseline rate of oxygen consumption ceases to be maintained.

"Decay line" refers to the variation of oxygen consumption with $pO_2$ which results at the lowered $pO_2$ levels (in non-drug conditions, always linearly decreased with decreasing $pO_2$).

General Description of the Method

In the present invention, the function that describes the adaptation of oxygen consumption to accomodate a sequential variation in a physiological stress is used as an index of the metabolic capacity of the animal. Ordinarily, this function describes the behavior of the rate of oxygen consumption in response to stress.

The rate of oxygen consumption reflects the ability to focus metabolically limited energy supplies in order to sustain work critical for survival. Natural selection has evolved highly structured metabolic controls which optimize energy utilization under many possible stress situations. The suite of metabolic adjustments available to compensate for each increasing increment of stress should be characteristic of each species and of the overall metabolic capacity of each individual organism. The invention describes an apparatus and methodology for measuring the adaptive response of an animal to stress and relates this adaptive response to the metabolic status of the entire animal. These adaptive adjustments reflect the general metabolic status of the animal because they are integrated into the dynamic operation of the entire physiological system. Metabolic dysfunctions should therefore change the pattern of these adjustments. Adaptive respiratory functions should therefore be sensitive to dysfunctions in anaerobic as well as aerobic processes since losses in anaerobic capacity will result in changes in the adaptive hypoxic response pattern.

While the mechanisms by which the metabolic rate of specific tissues is altered in response to stress conditions is not well understood, it is clear that these mechanisms are intimately integrated into the total metabolic response of the animal. This reasoning indicates that the pattern of adaptive respiratory responses that describe physiological adjustments to stress should be responsive to dysfunctions in these integrating processes as well as dysfunctions in organs, tissues and aerobic and anaerobic metabolic pathways.

The patterns that describe these adaptive respiratory changes therefore also assess the metabolic status of animals, humans and other organisms. In the method of the present invention, metabolic status is measured by generating functions which quantitate adaptive respiratory changes as a function of changes in stress. More than one stress factor may be applied simultaneously, for example, the adaptation of oxygen consumption of mice or other mammals is measured to varying degrees of hypoxia (i.e. a decrease in the partial pressure of oxygen) at a constant level of exercise. Conversely, the method of the invention also includes measuring the adaptation of oxygen consumption of mammals to variations in exercise at a constant partial pressure of oxygen. Other forms of stress are applicable to the method of the invention as well. For example, the adaptive oxygen consumption of any respiring organism may be measured as a function of decreasing $pO_2$ at a constant temperature; and conversely the adaptive oxygen consumption may be measured at constant $pO_2$, but increasing or decreasing temperature. Various combinations of constant and variable stress factors, these stress factors including temperature, exercise, oxygen pressure, and administration of, for example, radiation, drugs, and chemicals are also included. Thus, the invention is directed to assessing metabolic status using as a criterion thereof a measured adaptive respiratory capacity in response to variation in combinations of stress factors.

Description of a Specific Embodiment of the Method

In a specific embodiment of the method of the invention, the workload is held constant while the $pO_2$ is sequentially lowered.

Individual organisms maintain a baseline rate of oxygen consumption under normal standardized conditions of physical activity. When subjected to stress, conveniently administered in the form of a decreased $pO_2$ in the environment, the ability to maintain the baseline rate of oxygen consumption is at some point lost (i.e., the breakpoint), and a decrease in the rate of oxygen consumption occurs while the level of exercise (or workload) is maintained. This decrease appears to be linear with the diminution of $pO_2$ once the ability to maintain the baseline oxygen consumption has been lost (the decay line). Both the stress level (i.e., the $pO_2$) at which this change occurs, and the slope of the linear decrease appear to be related to the overall metabolic efficiency of the organism. In general, different organisms of the same species which have higher respiratory capacity i.e. better metabolic status, continue to maintain the baseline oxygen consumption level at lower oxygen concentrations, and the slope of the regression that describes the declining consumption of oxygen is lower. In addition, animals with higher respiratory capacity are capable of continuing to exercise at higher stress levels, typically lower partial pressures of oxygen. That is, they do not "fail" as easily.

Thus, when the respiratory capacities of organisms of a particular species are compared, the function that describes the adaptive respiratory response of the individual with the higher capacity (indicating improved metabolic status) will be characterized by three features: The animal will maintain the baseline level of oxygen consumption to a lower $pO_2$, the consumption of oxygen will decrease at a rate slower than that for organisms with lower capacities, i.e., the slope of the decay line will be less, and the animal will fail only at higher levels of stress. Since all three of these parameters can be quantitated, the method provides a rigorous method for measuring the overall respiratory capacity of the organism.

Further, measurement of changes in the adaptive respiratory responses can be used to assess the effects of drugs, toxicants or other treatments which are administered to the experimental subject. While, many toxicants or drugs may result in what appears to be a loss of respiratory capacity or decline in the function representing the index of metabolic status, i.e., the break point is encountered sooner and the decay line has a steeper slope, it is not predictable that this will in every case be, in fact, the observed result. Some toxicants, for example, dinitrophenol (DNP) exert their toxic effects in association with increases in oxygen consumption. In such cases, therefore, the curve will be distorted by virtue of the physiological mechanism causing the metabolic dysfunction. Therefore the function that describes the adaptive respiratory response of treated animals may also contain information that reflects the mechanisms of their physiological effects. The sensitivity of the technique to discern dysfunctions as an effect of drug or toxicant dose increases with the magnitude of the stress, i.e., low oxygen concentrations. Therefore, an empirical quantitative framework must be established in each individual case, as a calibration of the technique.

General Description of the Apparatus

In general, the apparatus employed by the method of the invention provides a means for stressing and monitoring the rate of oxygen consumption in an organism. The device ultilizes a polarographic oxygen sensing electrode and an electrolysis cell attached to a sealed chamber in which the biological material is placed. The current from the oxygen sensing electrode is proportional to the partial pressure of oxygen within the chamber and is compared to a reference voltage which may be adjusted according to the desired level of oxygen pressure within the chamber. When oxygen is consumed by the organism, the concentration of oxygen decreases within the respirometer causing the output from the electrode to decrease linearly. A comparator then perceives a difference between the oxygen sensing electrode output voltage and the preset reference voltage (which is set to maintain the oxygen concentration at a predetermined value) and closes the direct current circuit to the electrolysis cell. Oxygen then flows from the electrolysis cell to the sealed chamber while the hydrogen produced from the cell is ducted to a gas vent. As oxygen flows into the chamber, the polarographic electrode increases its current output until it equals the preset reference voltage. The comparator then terminates the current to the electrolysis cell. In addition carbon dioxide absorbant is provided to remove carbon dioxide from the chamber.

In performing the method of the invention, the testing chamber is brought to the desired oxygen concentration by introducing pure nitrogen gas while maintaining equilibration with atmospheric pressure. When the desired oxygen percentage is obtained, the testing chamber is closed off from the atmosphere and, as described above, remains capable of material exchange only with the oxygen generated from the electrolysis cell and with the carbon dioxide absorbant. At the preset $pO_2$, the oxygen consumption is measured by calculating the moles of oxygen consumed based on a straightforward Faraday calculation based upon the coulombs of electricity consumed by the electrolysis cell. The polargraphic electrode $pO_2$ reading and the ammeter reading, can be conveniently fed to standard data reduction systems which produce displays of oxygen consumption versus time, $pO_2$ and/or several of the stress parameters. The pattern thus produced is diagnostic of the metabolic state of the organism.

One advantage of the above-described system is that the test organism is completely free of the monitoring apparatus. As such, test results for any applied stress are independent of interference factors or stress factors which may be caused by encumbering the organism with a breathing mask and other monitoring equipment.

A further advantage of the present system also stems from the freedom of the test organism from the monitoring device in that such a system is highly flexible and allows the metabolic analysis of a great variety of organisms ranging from humans to other animals, seeds, embryos, unicellular organisms and gametes. Biological chambers that simultaneously test more than one animal at a time produce data reflecting the sum of the responses of the animals. Such data is ideal for screening programs.

Such a wide range of organisms is also uniquely testible in this invention because the device requires no minimum threshold level of air flow in order to operate. Instead, the supply of oxygen is accurately monitored and controlled through the combination of the oxygen sensing electrode and the electrolysis cell. Such control is achieved simply by recording the flow of electrons to the electrolysis cell through its direct current supply circuit.

The sensitivity of the device is a function of the sensitivity of the oxygen probe combined with the volume of the biological chamber. Small organisms should be tested in minimally sized chambers utilizing sensitive oxygen probes. The present probe has a sensitivity of 0.1% oxygen in air and 0.1 ppm oxygen in $H_2O$. A further advantage of the present invention is that the oxygen sensing elecrolysis cell combination for monitoring the consumption of oxygen to the organism can also be used to stress the organism by controlling the available partial pressure of oxygen through adjustments made to the reference voltage.

Finally, since the oxygen monitoring, generation and stressing components of this invention are electronic, the device can be highly automated. Models are envisioned where stress protocols are programmed into microcomputers, which then operate the system. The data can also be collected electronically and processed or stored as appropriate. Such systems are but modular refinements of the system described herein.

Description of the Apparatus of a Preferred Embodiment

FIG. 1 is a schematic of a preferred embodiment of the apparatus of the invention. In this embodiment, the oxygen consumption of an organism is measured while varying the available partial pressure of oxygen.

The essential elements of the apparatus are a testing chamber, a means to pre-set the oxygen pressure in the testing chamber, an oxygen sensor connected through a feedback circuit to an oxygen generator, and means to ascertain the amounts of oxygen generated to maintain the oxygen in the testing chamber at the pre-set level.

In the preferred embodiment, the testing chamber also contains a rotor to provide, optionally, a measured stress (exercise) on the part of an experimental subject. This feature is appropriate, of course, only for mobile subjects. Alternate measured stresses such as heat can be substituted for exercise as appropriate.

The oxygen pressure in the chamber is preset by exchanging the air in the chamber with a nitrogen stream to reduce the level of oxygen to that desired, and providing for the maintenance of this level by setting the feedback circuit to trigger at the proper level.

The oxygen sensor is a polarographic electrode which operates the feedback circuit. The oxygen generator is an electrolytic cell which decomposes water in response to the feedback circuit.

As shown in FIG. 1, the testing chamber 12 is provided with a door 13 attached by hinge 15 which permits access to experimental subjects. Gas exchange is facilitated by two manual valves, (not shown) which are opened when $N_2$ or $O_2$ respectively are introduced to adjust the partial pressure of oxygen, and closed to seal the chamber. Bolt 14 seals chamber door 13 to chamber 12 by compressing rubber gasket 16, which frames the door to give an air-tight seal. The chamber is also provided with a carbon dioxide absorbant (not shown).

The fan propeller 26 is driven by electric motor 25 which is magnetically coupled to the propellor to keep any heat generated by the motor outside of the chamber. The fan assures even circulation of the oxygen in the chamber.

A rotor 22 which provides mandated exercise is driven by the external motor 24.

Polarographic oxygen sensor 17 is threaded through the chamber wall. Polarographic oxygen sensors for measuring the percentage of oxygen present in a gas are well known in the art and are commercially available. U.S. Pat. No. 3,071,530 discloses one embodiment of a polarographic oxygen sensor. Since these oxygen sensors are generally temperature dependent, many commercially available units have a thermistor temperature-sensing element incorporated into the support structure of the oxygen sensing element so that temperature variations in the output current of the oxygen sensor may be compensated in the feedback control loop. Such a temperature compensation loop has been incorporated into the present system.

Figure 1A:
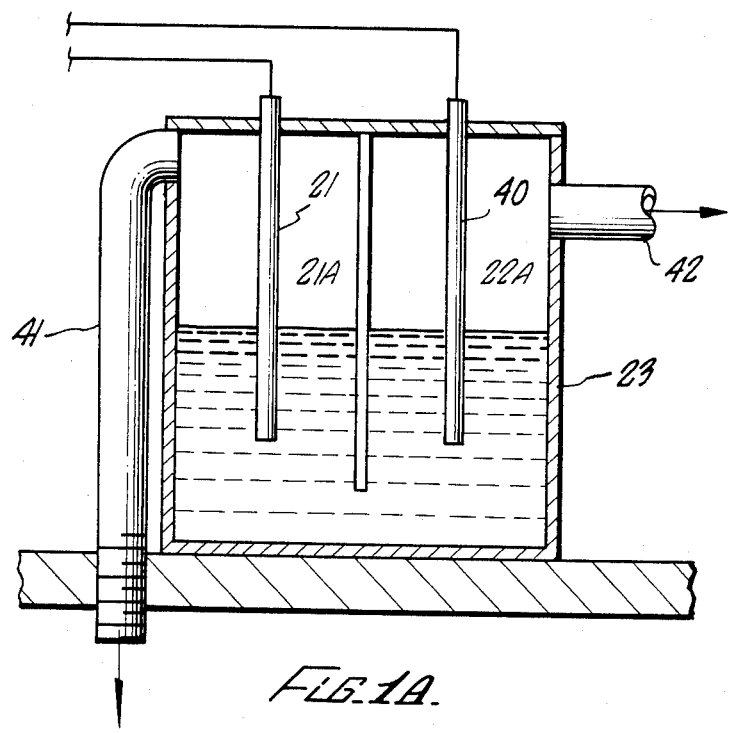
FIG. 1A is a schematic, and partial section view, illustrating an electrolysis cell.

The space above the oxygen generating electrode of the electrolysis cell 23 is also in communication with the testing chamber. FIG. 1A shows the electrolysis cell. It contains a dilute aqueous solution suitable for electrolysis such as, for example, 4 N sulfuric acid, into which are submerged electrodes anode 21 and cathode 40. Space 21A communicates with chamber interior 35 via oxygen line 41. Space 22A vents hydrogen to the out of doors via vent 42.

As shown in FIG. 1, polarographic oxygen sensor 17 is connected in series with DC power supply 37 and comparator 18.

DC power supply 38 is in series with variable resistor 32 and comparator 18. Relay power supply 39 is in series with comparator 18 and relay 19.

Ammeter 27 is in series with electrolysis cell 23 and DC power supply 20. The readout from the ammeter 27 is displayed on a plotter 28.

The device is operated by placing an organism into the testing chamber. The chamber door 13 is then closed forming an airtight seal by tightening bolt 14 and compressing gasket 16. The desired oxygen mixture is then introduced into the chamber and the oxygen concentration is confirmed by an oxygen meter or other independent means.

The desired partial pressure of oxygen within the testing chamber is maintained by setting the variable resistor 32 such that the reference voltage within comparator 18 just equals the signal from the oxygen sensor 17.

As oxygen is consumed by the organism, the output current of polarographic oxygen sensor 17 decreases. When the output current of polarographic oxygen sensor 17 falls below the preset reference value of comparator 18, the comparator operates relay switch 19 which actuates the relay switch to the DC power supply circuit 20. The DC voltage applied by circuit 20 operates the electrolytic cell producing oxygen on the surface of anode 21 and hydrogen on the suface of cathode 40. The hydrogen gas produced by cathode 22 is disposed of through vent 42 to the atmosphere. The oxygen is released into the testing chamber interior via oxygen line 41.

As the partial pressure of oxygen rises in the testing chamber, polarographic oxygen sensor 17 again increases its output current until it equals the preset reference value of comparator 18. Comparator 18 then opens relay switch 19 thus terminating the supply of current to the electrolysis cell. Thus, through the feedback loop comprising polarographic oxygen sensor 17, comparator 18, relay switch 19, and electrolysis cell 23, any desired value of partial oxygen pressure within chamber 12 can be maintained during respiratory communication or altered by varying the preset reference voltage of comparator 18.

The amount of oxygen generated to replace that consumed by the experimental subject is calculated by measuring the current flowing through the electrolysis cell.

The electrolysis cell decomposes water into its elements and the oxygen generated in quantitavely related to the total current flow according to the laws of electrochemistry as defined by Farady, Nernst and Butler - Volmer. The accuracy and precision measurement is dependent upon the measurement of the current flowing between the electrodes and the purity of the electrolyte. Accurate and precise measurements are easily obtained.

Applying the above relationships, it can be shown that during the electrolysis of water 0.2984 grams of oxygen are liberated per amphere hour (Ah). The current supplied to the electrolysis cell of the device described herein can be varied from 0-8 AhDC. The present electronics package is capable of running four such systems simultaneously. Each respirator can therefore produce a maximum of 39.79 mg $O_2$ per minute.

The operation of this preferred embodiment is further illustrated in the examples below, which are presented to illustrate, rather than limit the invention.

In all of the examples below, the results are plotted with time as at least an alternative abscissa on the pattern resulting. In each case, each point on the graph represents the average values of oxygen consumed over the previous 15 minutes from the time shown. That 15 mimutes is always the 15 minutes spent from the experimental subject in the testing chamber under measurement conditions. Times which are spent in adjusting oxygen concentrations, or in removing the animals for dosage or other manipulation do not appear in the abscissa line of the resulting plots. Since these removal times and adjustment times may have some impact on the response of the subject, experiments which are compared are performed to rigorously timed protocols. For example, the tests run in Examples 2 and 3 are intended to be compared to each other. Therefore, the time allotted to decrease the oxygen pressure in the testing chamber by adjusting the ratio of nitrogen to oxygen as there described is standardized as between the two Examples.

EXAMPLE 1

Respiratory Rates of Exercising Untrained Mice

Three Balb-C mice, eight weeks old, which had not been previously conditioned were placed in the testing chamber of the apparatus shown schematically in FIG. 1. The chamber was turned at a rate of 6 rpm which was equivalent to a speed of 228 meters per hour. A total of 9 animals were used in three experimental runs conducted on the same day, three mice being used per run. This test was then repeated with animals exercising at 15 rpm (570 m/hr).

The oxygen concentrations ($pO_2$) expressed as a percentage of oxygen in the gas mixture was maintained at ambient pressure and at 21 percent oxygen concentration throughout these first experiments. The respiration rate which is measured in mg oxygen per hour per gram is plotted on the y-axis. Each point on the curve represents the average respiration rate over the previous 15 minutes.

Figure 2:
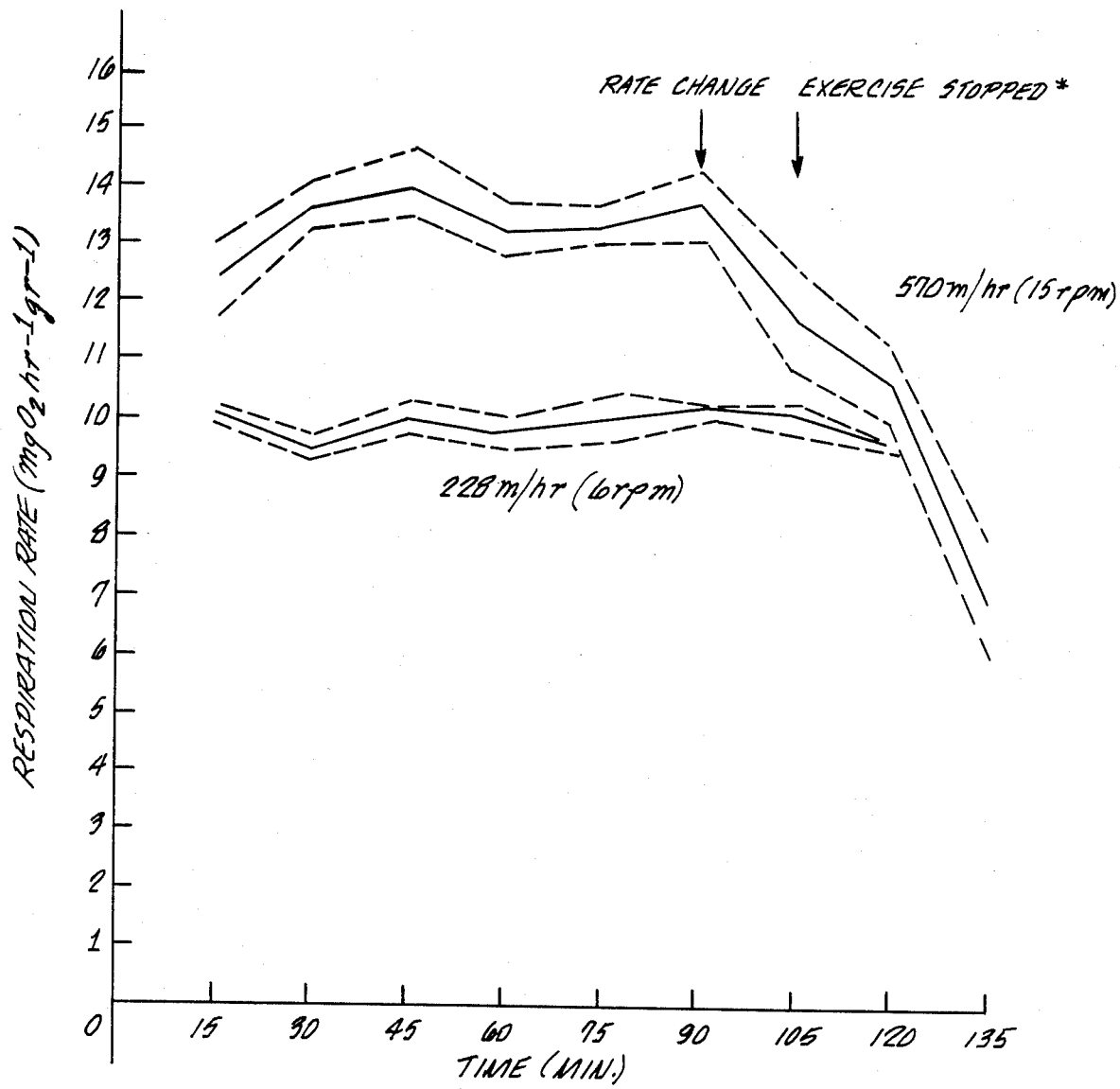
FIG. 2 compares the oxygen consumption rates at two different levels of exercise in mice.

As seen in FIG. 2, a baseline oxygen consumption value was established at approximately 9.5 and 13.5 mg oxygen per hour per gram for animals exercising at 228 m/hr and 570 m/hr respectively. The dotted lines on the Figure represent one standard deviation from the mean value. Animals exercising at the 228 m/hr rate maintained the exercise and respiratory rate for two hours at which time the experiment was terminated. Animals exercising at 570 m/hr began lowering their respiratory rate after 90 mintes of exercise. After 105 minutes these apparently fatigued animals were rested.

EXAMPLE 2

Metabolic Status of Untrained Mice

Three Balb-C mice, eight weeks old, which had not been previously conditioned were placed in the testing chamber of the apparatus shown schematically in FIG. 1. The chamber was turned at a rate of 6 rpm which was equivalent to a speed of 228 meters per hour. A total of 9 animals were used in three experimental runs conducted on the same day, three mice being used per run. The results as shown in FIG. 3 are the average of the three experimental runs.

Figure 3:
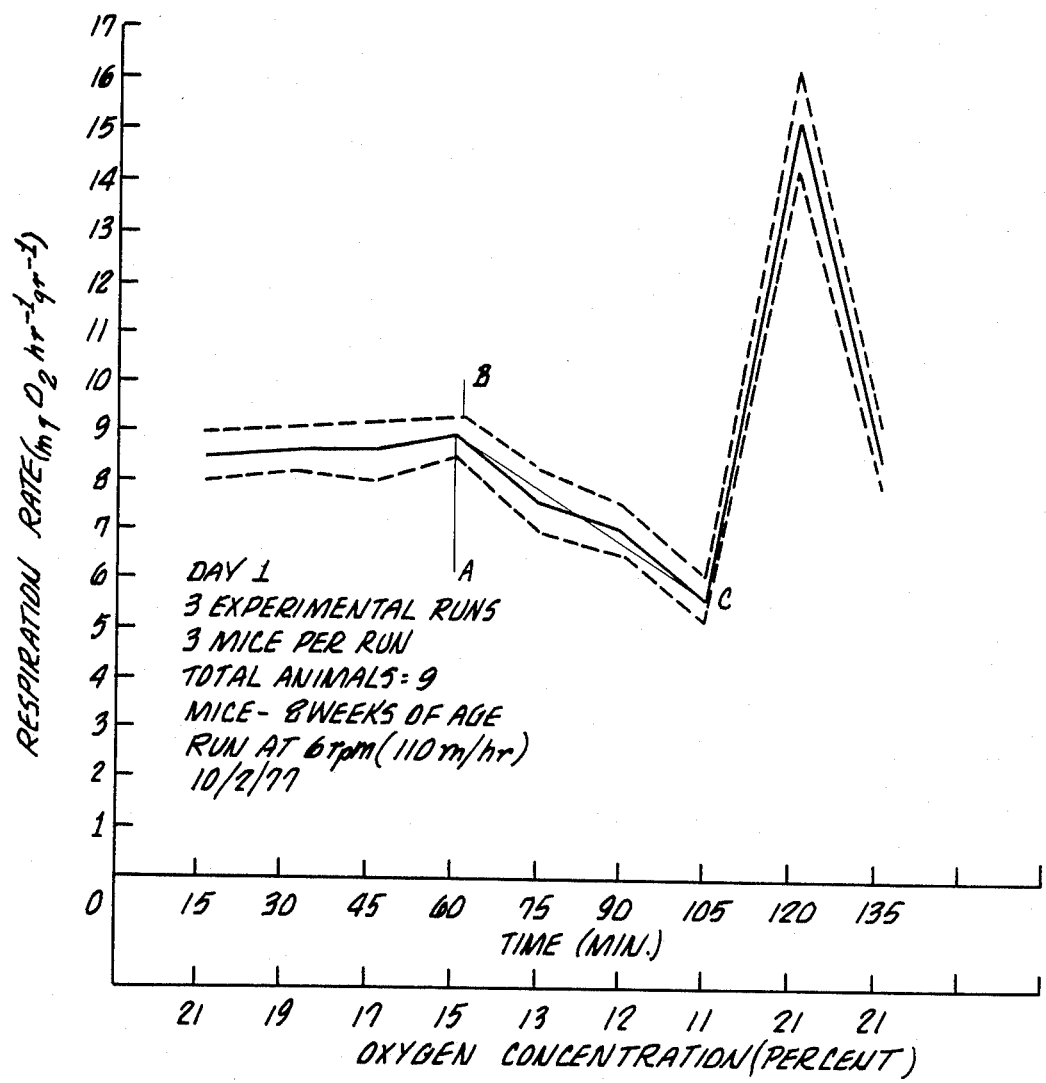
FIG. 3 is a graph showing the effect of reduced oxygen pressure on untrained mice.

The oxygen concentrations ($pO_2$) expressed as a percentage of oxygen in the gas mixture which is kept at ambient pressure is plotted on the x-axis of the graph shown in FIG. 3. The respiration rate which is measured in mg oxygen per hour per gram is plotted on the y-axis. Each point on the curve represents the average over the previous 15 minutes at which the $pO_2$ was held at the value shown.

As seen in FIG. 3, a baseline oxygen consumption value was established at approximately 8.5–9.0 mg oxygen per hour per gram. (The dotted lines on the Figure represent one standard deviation from the mean value.) When the oxygen concentration was lowered to 15%, the oxygen consumption began to decline in a roughly linear fashion, within experimental error, until the animals "failed to exercise" at which time the pressure of oxygen was increased to a concentration of 21%. The oxygen consumption of these resting, fatigued mice then increased and decayed describing a curve crudely described in FIG. 3. The area under this curve is a measurement of the anaerobic respiratory capacity of the animal. Minor electrical refinements to the device described herein will allow the accurate measurement of this anaerobic capacity using this technology.

The relevant quantitation of the results is as follows: The breakpoint occurred at 15% oxygen concentration, the slope of the decay line of the respiration rate as 1.0 mg $O_2$ hr$^{-1}$ gr$^{-1}$ for each percent decrease in $pO_2$ between 15 and 11 percent $O_2$ under the conditions of this experiment. Similar parameters can be calculated relating the decrease in respiration rate as a function of time after the breakpoint. As shown in FIG. 3, slope of the decay line for the respiratory rate is 0.066 mg hr$^{-1}$ gr$^{-1}$ for each minute between 60 and 105 minutes.

Using the protocol described, animals became exhausted after exercising at 11% oxygen and 105 minutes.

EXAMPLE 3

Metabolic Status of Trained Mice

Figure 4:
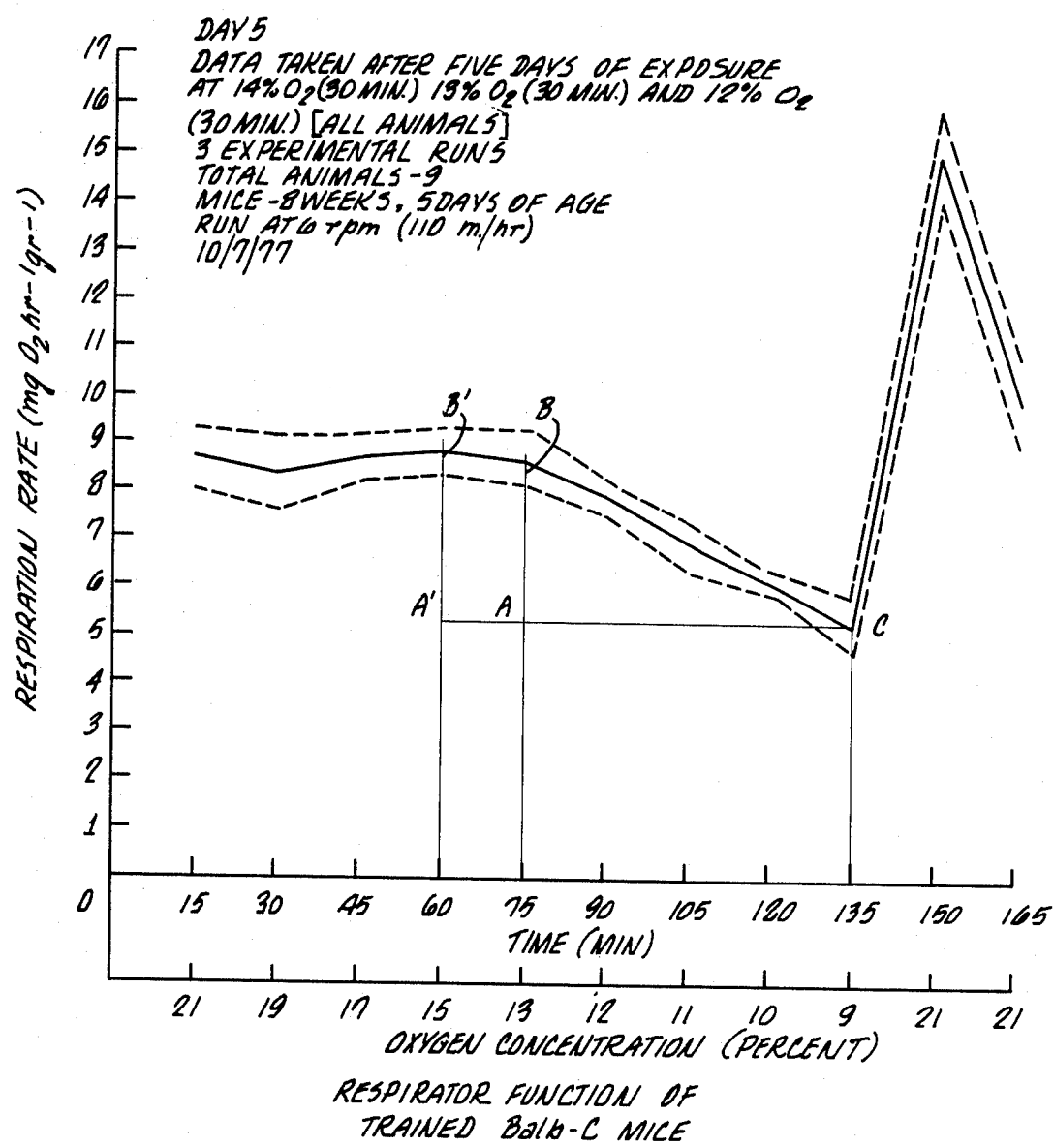
FIG. 4 is a graph showing the effect of reduced oxygen pressure on conditioned mice.

The same mice which were used in Example 2 were tested after having been subjected to a "training program" which consisted of five days during which the animals were exposed to atmospheres of 14%, 13% and 12% oxygen for thirty minutes each while exercising at 228 m/hr. The metabolic status test was run under the same conditions as set forth in Example 2 and the results are set forth in FIG. 4. The results indicate that the same initial respiratory rate of 8.5 my oxygen per hour per gram was established. However, the consumption of oxygen did not begin to decrease until an oxygen concentration of 13% was reached. The rate of decrease in conditioned animals was slower than in the untrained mice tested in Example 2. The consumption of oxygen decreased at a rate of 0.6 mg $O_2$ $hr^{-1}$ $gr^{-1}$ compared to 1.0 mg $hr^{-1}$ $gr^{-1}$ for each percent decrease in $pO_2$, as reported above. Similarly, decrease in oxygen consumption as a function of time was lower in conditioned animals, 0.033 vs 0.066 mg $hr^{-1}$ $gr^{-1}$ for each minute between sixty minutes and failure to exercise.

EXAMPLE 4

Effect of Lowered $pO_2$ on Toxicant Effects

Figure 5:
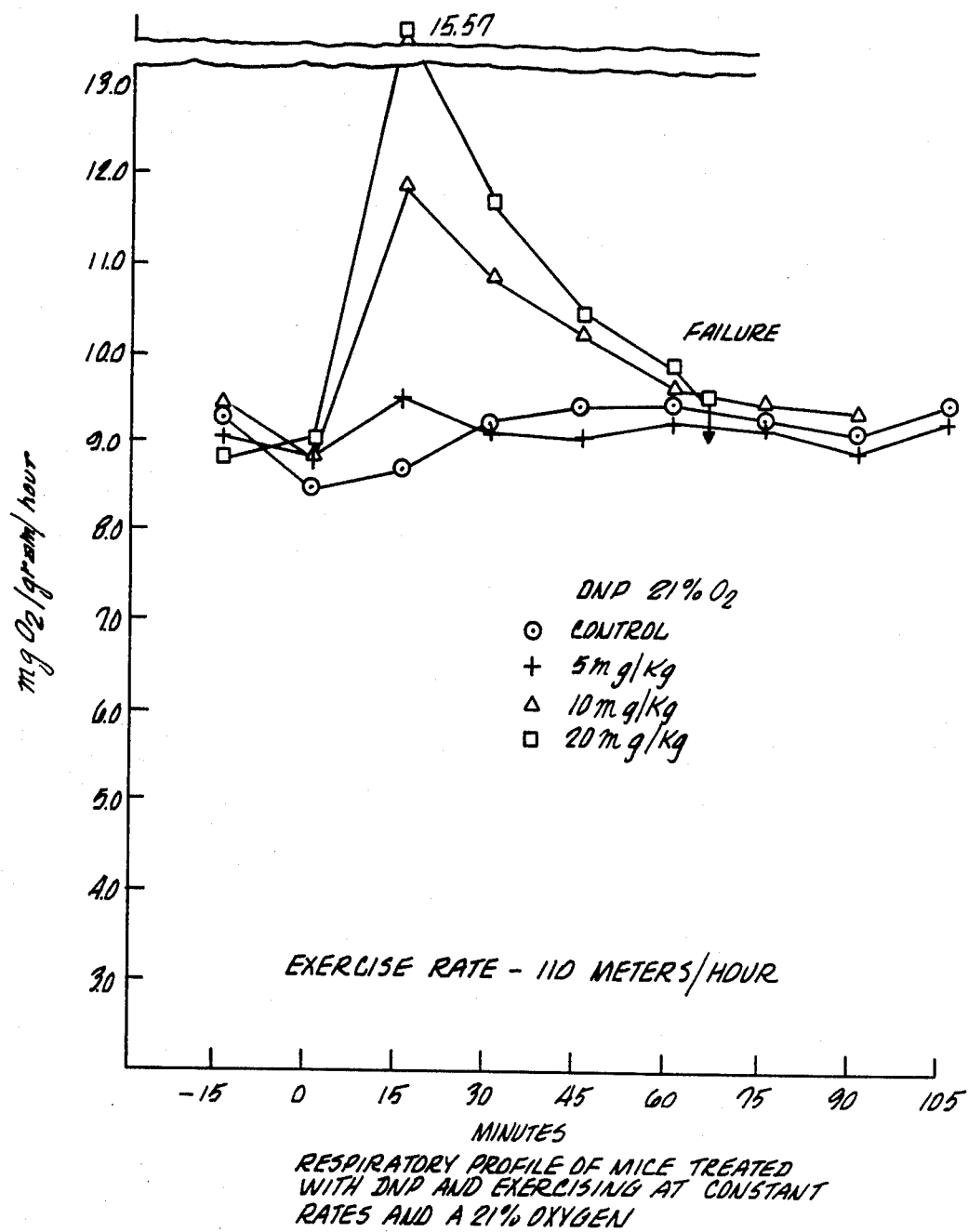
FIG. 5 is a graph which compares the effects of various DNP toxin dosage levels under 21% partial oxygen pressure.
Figure 6:
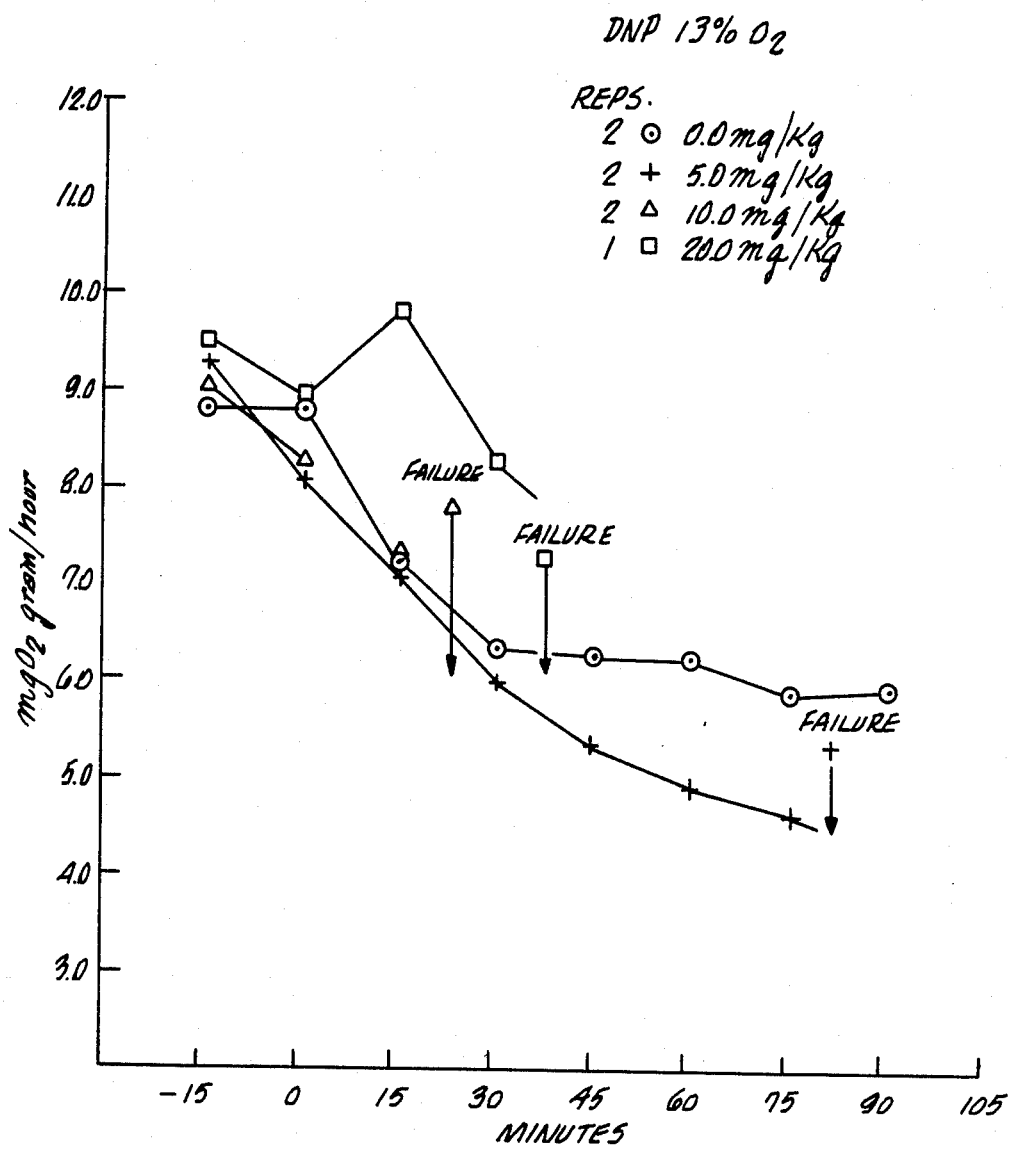
FIG. 6 is a graph which compares the effects, of various DNP toxin dosage levels under 13% partial oxygen pressure.

The effects of dinitrophenol (DNP) a known uncoupler for oxidative phosphorylation were tested on mice both at normal oxygen concentration (21%) and at lower oxygen concentration (13%). FIGS. 5 and 6 show the results of testing this toxicant at the two levels of oxygen tension.

In the assay, 3 Balb-C mice were placed in the testing chamber of the apparatus shown in FIG. 1. The oxygen consumption was measured and DNP administered at zero time. As in the previous examples, the points shown on the curve represent the average respiration rates of the previous fifteen minute interval. Therefore, the points at −15 and 0 in FIGS. 5 and 6 represent non-dosed oxygen consumptions. As shown in FIG. 5, the effect of DNP is to increase the rate of oxygen consumption dramatically. As would be expected, the effect is greater at high dose concentrations i.e., 20 mg/kg than at lower ones i.e., 10 mg/kg. At 5 mg/kg, the effect becomes undetectable within experimental error. Only the mice given 20 mg/kg DNP failed during the 105 minutes that the experiment was conducted. The results presented in FIG. 5 are consistent with classic data concerning this well studied toxicant.

The effect of the drug becomes more pronounced if the experiment was rerun at 13% oxygen as shown in FIG. 6. The data presented in FIG. 6 were obtained by placing animals in the respirometer at 21% oxygen and exercising them as in FIG. 5 for the 15 and 0 time intervals. The animals were them removed, dosed, replaced in the respirometer and exercised at a $pO_2$ of 13% oxygen.

As would be expected, at the lower 13% oxygen concentrations the respiration rate of control animals decreases as did that of similarly treated animals reported in FIG. 3. The animals receiving DNP at any dose level follow altered curves from that under 21% oxygen (FIG. 5) as would be expected since at an oxygen concentration of 13%, the cardiovascular system cannot supply the oxygen necessary for these high consumption rates. However, at 13% oxygen concentration all toxicant dosages including the 5.0 mg/kg dosage cause animals to fail to perform their exercise protocols. This latter dosage is indistinguishable from the control when conventional respiratory techniques are used.

I claim:

1. A method of measuring metabolic status of an organism which comprises:
    (a) subjecting the organism to variation in the intensity of stress resulting from a combination of stress factors;
    (b) measuring the rate of oxygen consumption of the organism at said varying intensity of stress;
    (c) generating a pattern of variation of oxygen consumption in (b) as a function of variation in stress in (a); and
    (d) evaluating said pattern,
    wherein the organism is subjected to a second stress factor, different in type from that employed in (a) during the process of (a) and (b), and wherein said second stress factor is applied at a constant level.

2. The method of claim 1 wherein the organism is subjected to varying levels of stress by varying the $pO_2$ to which said organism is exposed.

3. The method of claim 1 wherein a second stress factor is exercise.

4. The method of claim 1 which includes the step of subjecting the organism to a third stress factor during the conduct of steps (a) and (b).

5. The method of claim 4 wherein the third stress factor is subjecting the organism to a toxin.

6. A process for measuring the metabolic status of an organism which comprises:
    (a) subjecting the organism to varying levels of stress of a first type while simultaneously subjecting the organism to a constant level of stress of a second type;
    (b) measuring the rate of oxygen consumption of the organism at said varying levels of stress of the first type;
    (c) generating a pattern of variation of oxygen consumption of the organism at the varying levels of stress of the first type;
    (d) evaluating said pattern.

7. The method of claim 6 wherein the stress of the first type is imposed by varying levels of the $pO_2$ to which the organism is subjected.

8. The method of claim 7 wherein the stress of the second type is exercise.

9. The method of claim 7 wherein the stress of the second type is heat or cold.

10. The method of claim 7 wherein the stress of the second type is administration of a drug.

11. The method of claim 7 wherein the stress of the second type is administration of radiation.

12. The method of claim 7 wherein the stress of the second type is administration of a chemical.

13. The method of claim 6 wherein the stress of the first type is imposed by varying the amount of exercise required of the subject and the stress of the second type is constant decreased $pO_2$.

14. The method of claim 6 wherein the stress of the first type is imposed by varying the temperatures and the stress of the second type is lowered $pO_2$.

15. The method of claim 6 wherein the stress of the first type is imposed by varying the dosage level of a drug and the stress of the second type is lowered $pO_2$.

16. The method of claim 6 wherein the stress of the first type is imposed by varying the dosage level of radiation and the stress of the second type is lowered $pO_2$.

17. The method of claim 6 wherein the stress of the first type is imposed by varying the dosage level of a chemical and the stress of the second type is lowered $pO_2$.

18. The method of claim 6 or 7 which includes the step of subjecting the organism to a third type of stress during the conduct of step (a) and (b).

19. An apparatus for measuring metabolic status of an organism which comprises:
(a) a means for subjecting said organism to variation in the intensity of stress resulting from a combination of stress factors;
(b) a means for measuring the oxygen consumption of said organism with variations in the intensity of each stress factor;
(c) a means for generating a pattern of variation of oxygen consumption in (b) as a function of variation of stress in (a); and
(d) a means for evaluating said pattern, wherein the means for subjecting the organism to stress is a means for controlling the partial pressure of $O_2$.

20. The apparatus of claim 19 wherein the means for controlling the partial pressure of $O_2$ is a feedback circuit controlling an oxygen generator.

21. The apparatus of claim 20 wherein the feedback circuit includes a polarographic oxygen sensor.

22. The apparatus of claim 19 wherein the means of measuring oxygen consumption is an ammeter in series with an electrolytic oxygen generator.

23. A method of determining physiological status of an organism, which method comprises subjecting the organism to a series of oxygen ambient pressures, measuring the rate consumption of oxygen by the organism at each pressure and correlating the oxygen consumption with the ambient pressure.

24. The method of claim 23 wherein the series of oxygen ambient pressures is a series of decreasing pressures.

25. The method of claim 24 wherein the correlation consists in plotting oxygen pressure against rate of oxygen consumption.

26. The method of claim 24 wherein the organism is additionally subjected to stress of a form other than that of reduced $pO_2$.

27. The method of claim 26 wherein the organism is a mammal and the additional stress is exercise.

28. A method of determining physiological status of an organism, which method comprises placing the organism in a respirometer, supplying oxygen to maintain a preset level of oxygen pressure in the respirometer, monitoring the amount of oxygen required to be supplied to maintain said preset level, and generating a correlation between the amount of oxygen supplied and the level of preset oxygen pressure at a measure rate of exercise, wherein said rate of exercise is measured by a rotor contained within said respirometer and conn-nected to an external motor, wherein the level of oxygen pressure is progressively lowered.

* * * * *

UNITED STATES PATENT AND TRADEMARK OFFICE
CERTIFICATE OF CORRECTION

PATENT NO. : 4,724,845
DATED : October 25, 1988
INVENTOR(S) : Richard A. Callahan It is certified that error appears in the above-identified patent and that said Letters Patent are hereby corrected as shown below:

On the cover page, in the left hand column, item [73], change the assignee from "Vestar Research, Inc." to --Vestar, Inc.--

On the cover page, the left hand column, item [63], line 3, change "Aug. 13, 1983" to --Aug. 13, 1982--.

In the specification, column 1, line 8, change "1983" to --1982--.

Signed and Sealed this

Eleventh Day of April, 1989

*Attest:*

DONALD J. QUIGG

*Attesting Officer*    Commissioner of Patents and Trademarks